US011717632B2

(12) United States Patent
Kabumoto et al.

(10) Patent No.: US 11,717,632 B2
(45) Date of Patent: Aug. 8, 2023

(54) AIRWAY ADAPTOR AND NASAL CANNULA

(71) Applicant: NIHON KOHDEN CORPORATION, Tokyo (JP)

(72) Inventors: Kenichiro Kabumoto, Tokyo (JP); Takayuki Aoyagi, Tokyo (JP); Fumihiko Takatori, Tokyo (JP); Masayuki Inoue, Tokyo (JP)

(73) Assignee: NIHON KOHDEN CORPORATION, Tokyo (JP)

(*) Notice: Subject to any disclaimer, the term of this patent is extended or adjusted under 35 U.S.C. 154(b) by 1183 days.

(21) Appl. No.: 16/352,118

(22) Filed: Mar. 13, 2019

(65) Prior Publication Data

US 2019/0298960 A1 Oct. 3, 2019

(30) Foreign Application Priority Data

Mar. 29, 2018 (JP) ................................ 2018-064937
Nov. 21, 2018 (JP) ................................ 2018-218145

(51) Int. Cl.
| | |
|---|---|
| *A61M 16/08* | (2006.01) |
| *A61M 16/00* | (2006.01) |
| *A61M 16/06* | (2006.01) |
| *A61B 5/097* | (2006.01) |
| *A61B 5/08* | (2006.01) |

(Continued)

(52) U.S. Cl.
CPC .......... *A61M 16/085* (2014.02); *A61B 5/082* (2013.01); *A61B 5/0873* (2013.01); *A61B 5/097* (2013.01); *A61M 16/0003* (2014.02); *A61M 16/0672* (2014.02); *A61B 5/0059* (2013.01); *A61B 5/0836* (2013.01); *A61M 2205/3306* (2013.01);

(Continued)

(58) Field of Classification Search
CPC ...................... A61M 16/0666; A61M 16/0672
See application file for complete search history.

(56) References Cited

U.S. PATENT DOCUMENTS

| | | |
|---|---|---|
| 2004/0206907 A1 | 10/2004 | Yamamori et al. |
| 2005/0284484 A1 | 12/2005 | Curti et al. |

(Continued)

FOREIGN PATENT DOCUMENTS

| | | |
|---|---|---|
| JP | 2009-545408 A | 12/2009 |
| JP | 2012-010780 A | 1/2012 |
| JP | 2014-064881 A | 4/2014 |

OTHER PUBLICATIONS

Extended European Search Report issued in Patent Application No. EP 19 16 2754 dated Aug. 13, 2019.

(Continued)

*Primary Examiner* — Margaret M Luarca
(74) *Attorney, Agent, or Firm* — Pearne & Gordon LLP

(57) ABSTRACT

An airway adaptor includes: a nasal expiration collecting portion which is to be connected to a nostril of a living body, and which collects an expiration of the nasal cavity; a gas passage portion that forms a gas passage through which the expiration collected by the nasal expiration collecting portion passes; and a gas sensor attaching portion to which a gas sensor that is disposed in the gas passage portion, and that measures the concentration of a predetermined gas component contained in the expiration is attachable. The nasal expiration collecting portion shows a flowing state where a flow of the expiration is allowed, and an obstruction state where the flow of the expiration is blocked.

2 Claims, 10 Drawing Sheets

(51) Int. Cl.
  *A61B 5/087*  (2006.01)
  *A61B 5/00*  (2006.01)
  *A61B 5/083*  (2006.01)
(52) U.S. Cl.
  CPC .............. *A61M 2210/0618* (2013.01); *A61M 2210/0625* (2013.01); *A61M 2230/432* (2013.01)

(56) References Cited

U.S. PATENT DOCUMENTS

| | | |
|---|---|---|
| 2008/0190436 A1 | 8/2008 | Jaffe et al. |
| 2012/0209096 A1 | 8/2012 | Jaffe et al. |
| 2014/0066800 A1 | 3/2014 | Takatori et al. |
| 2014/0094669 A1 | 4/2014 | Jaffe et al. |
| 2014/0276169 A1 | 9/2014 | Chua |
| 2018/0064898 A1* | 3/2018 | Evans ................... A61M 16/14 |
| 2019/0175861 A1* | 6/2019 | Holyoake ......... A61M 16/0683 |

OTHER PUBLICATIONS

Japanese Office Action dated Aug. 30, 2022 issued in corresponding Japanese Patent Application No. 2018-218145.

* cited by examiner

AIRWAY ADAPTOR AND NASAL CANNULA

CROSS-REFERENCE TO RELATED APPLICATIONS

This application is based on and claims priority under 35 USC 119 from Japanese Patent Applications No. 2018-064937 filed on Mar. 29, 2018 and No. 2018-218145 filed on Nov. 21, 2018 the contents of which are incorporated herein by reference.

TECHNICAL FIELD

The presently disclosed subject matter relates to an airway adaptor and a nasal cannula.

BACKGROUND ART

As a tool for enabling high concentration oxygen to be inhaled through the oral cavity or the nasal cavity in order to perform a treatment for dissolving a hypoxic condition, an oxygen mask and an oxygen cannula are known. Moreover, an airway adaptor is known to which, in order to monitor the respiratory condition of the living body when a technique such as a surgery or a procedure is performed, a carbon dioxide concentration measurement sensor (hereinafter, referred to as "$CO_2$ sensor") for measuring the concentration of carbon dioxide contained in the expiration while causing oxygen to be inhaled through the oral cavity or the nasal cavity can be attached.

As a technique related to an airway adaptor, an airway adaptor has been disclosed that includes: a gas passage into which the respiratory gas of a subject flows; a nasal cannula which guides the respiratory gas emitted from the nostrils of the subject, to the gas passage; a mouth guide which guides the respiratory gas emitted from the mouth of the subject, to the gas passage; and an airway case on which a temperature sensor that detects a temperature change of the respiratory gas flowing into the gas passage is mountable (for example, see Patent Literature 1).

CITATION LIST

Patent Literature

Patent Literature 1: JP-A-2014-64881

SUMMARY OF INVENTION

In the case of a technique in which a tool is inserted into one of the two nostrils, such as a transnasal endoscopic surgical procedure, it is desired to simultaneously perform inhalation of oxygen and monitoring of the respiratory condition. In a conventional airway adaptor, two nasal cannulas which are to be inserted into the nostrils are disposed in accordance with the two nostrils. In such a case, therefore, the nasal cannula on the side of the nostril into which the tool is to be inserted impedes the implementation of the technique, and the airway adaptor is difficult to be used in adaptation to various techniques.

It is an object of the presently disclosed subject matter to improve the adaptabilities of an airway adaptor and a nasal cannula to techniques.

Solution to Problem

The presently disclosed subject matter provides an airway adaptor wherein the adaptor includes: a nasal expiration collecting portion which is to be connected to a nostril of a living body, and which collects an expiration of a nasal cavity; a gas passage portion that forms a gas passage through which the expiration collected by the nasal expiration collecting portion passes; and a gas sensor attaching portion to which a gas sensor that is disposed in the gas passage portion, and that measures the concentration of a predetermined gas component contained in the expiration is attachable, and the nasal expiration collecting portion shows a flowing state where a flow of the expiration is allowed, and an obstruction state where the flow of the expiration is blocked.

The presently disclosed subject matter provides a nasal cannula wherein the cannula includes a nostril connecting portion which is to be connected to a nostril of a living body, and which supplies a gas to a nasal cavity, and the nasal cavity connecting portion shows a flowing state where a flow of the gas is allowed, and an obstruction state where the flow of the gas is blocked.

According to the presently disclosed subject matter, it is possible to improve the adaptabilities of an airway adaptor and a nasal cannula to techniques.

BRIEF DESCRIPTION OF DRAWINGS

Hereinafter, embodiments of the airway adaptor and nasal cannula of the presently disclosed subject matter will be described with reference to the drawings. In the embodiments, the airway adaptor collects the expiration in order that the respiratory condition of the living body is monitored by a carbon dioxide concentration measurement sensor (hereinafter, referred to as "gas sensor") for measuring the concentration of carbon dioxide contained in the expiration emitted from the oral cavity or nasal cavity of the human body that is an example of the living body. In the embodiments, an airway adaptor which, in order to dissolve a hypoxic condition when a technique such as a surgery or a procedure is performed, monitors the respiratory condition of the living body while supplying oxygen to the oral cavity or the nasal cavity will be described. In the embodiment, the nasal cannula is a tool for, in, for example, a treatment for dissolving a hypoxic condition, supplying a gas (such as highly concentrated oxygen) from a tubular nostril connecting portion which is inserted into a nostril, to the nasal cavity.

In the following description and the drawings, it is assumed that the direction which, when the airway adaptor is attached to the human body that is an example the living body, is opposed to the face of the human body is the front direction, and the surface of the airway adaptor which is attached to the human body is the front surface. In the following description and the drawings, directions as seen in the front direction in the case where the airway adaptor is attached to the human body are assumed as follows: the left direction as viewed toward the face of the human body to which the airway adaptor is attached is the −X direction; the right direction as viewed toward the face is the +X direction; the direction which is directed toward the interior of the oral cavity of the human body is the +Y direction; the direction which is separated from the oral cavity of the human body is the −Y direction; the direction which is directed toward the upper side (the vertex) of the face of the human body is the +Z direction; and the direction which is directed toward the lower side (the jaw) is the −Z direction.

[First Embodiment]

Figure 1:
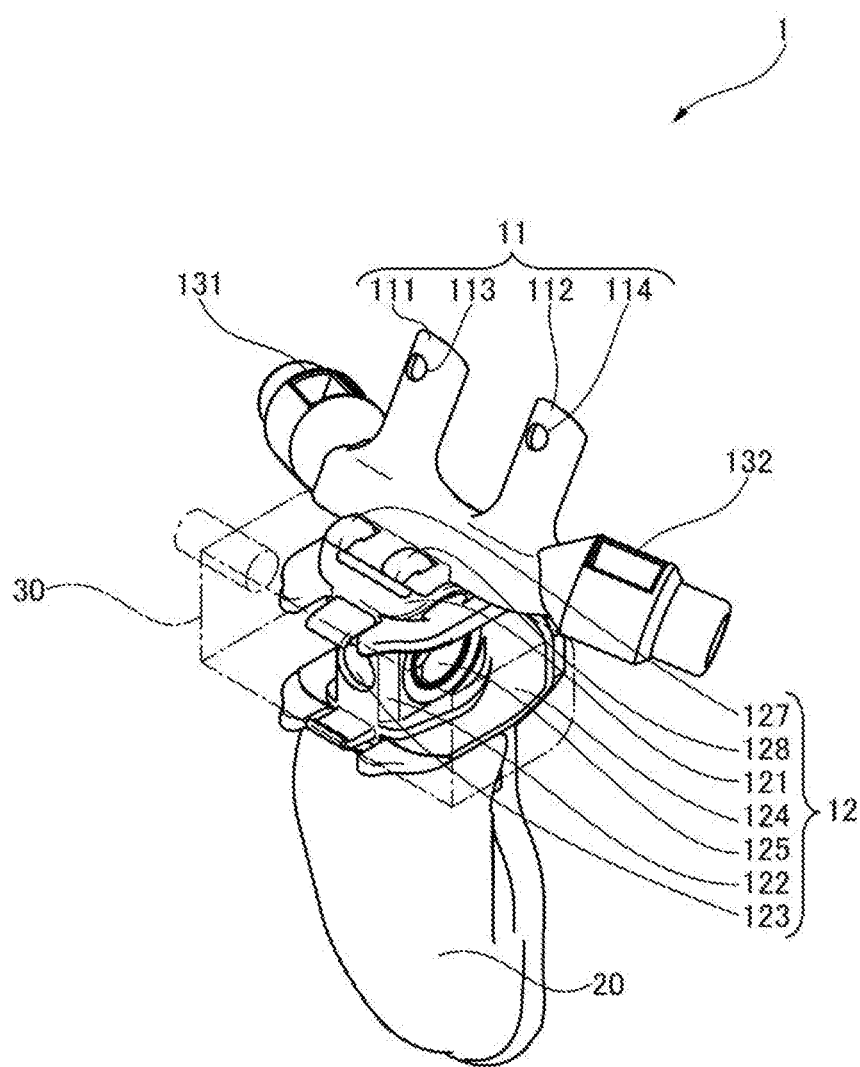
FIG. 1 is a perspective view illustrating a first embodiment of the airway adaptor of the presently disclosed subject matter.

FIG. 1 is a perspective view illustrating a first embodiment of the airway adaptor of the presently disclosed subject matter. As illustrated in FIG. 1, the airway adaptor 1 may include a nasal expiration collecting portion 11, a gas sensor attaching portion 12, a first gas supplying portion 131, a second gas supplying portion 132, and an oral expiration collecting portion 20.

In the airway adaptor 1, when the position where the gas sensor attaching portion 12 is disposed is set as the center, the nasal expiration collecting portion 11 extends in the +Z and +Y directions. The nasal expiration collecting portion 11 is formed by a material in which the degree of influence on the human body is low, and which is soft and flexible, such as a silicone resin.

The gas sensor attaching portion 12 is disposed below the nasal expiration collecting portion 11 in the −Z direction. As indicated by the dash-dot lines in FIG. 1, a gas sensor 30 can be attached to the gas sensor attaching portion 12 from the front surface in the +Y direction.

The first gas supplying portion 131 is disposed so as to extend in the −X direction with setting the position where the gas sensor attaching portion 12 of the airway adaptor 1 is disposed, as the center. The second gas supplying portion 132 is disposed so as to extend in the +X direction with setting the position where the gas sensor attaching portion 12 of the airway adaptor 1 is disposed, as the center.

The oral expiration collecting portion 20 is disposed so as to extend in the −Z direction with setting the position where the gas sensor attaching portion 12 of the airway adaptor 1 is disposed, as the center. When the airway adaptor 1 is attached to the face of the human body, the oral expiration collecting portion 20 is located in front of the oral cavity, collects the expiration emitted from the mouth, and sends the collected expiration to the gas sensor attaching portion 12.

Figure 2:
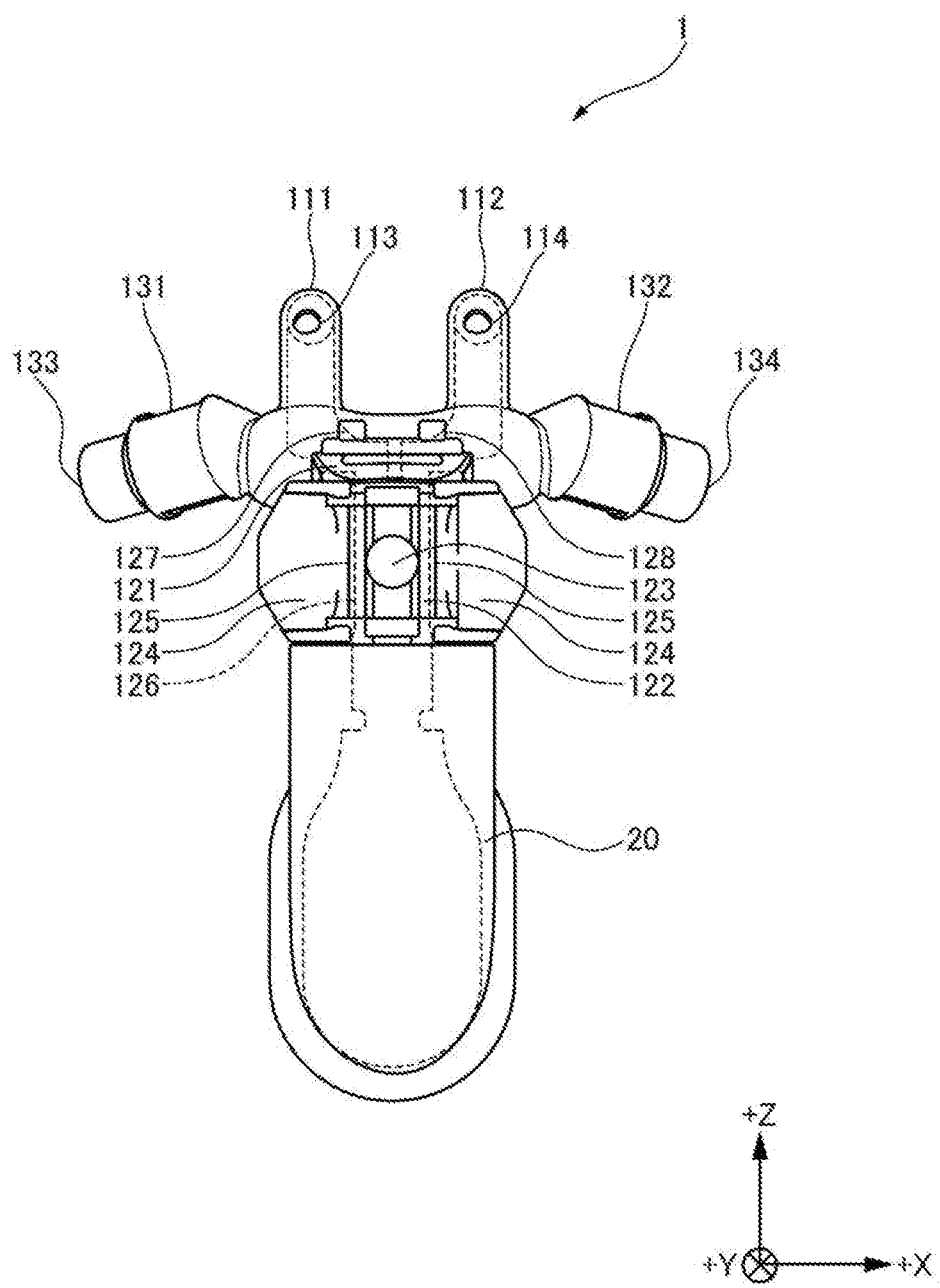
FIG. 2 is a diagram of the airway adaptor illustrated in FIG. 1, as viewed in the front direction.

FIG. 2 is a diagram of the airway adaptor 1 as viewed in the front direction. As illustrated in FIG. 2, in the upper part of the gas sensor attaching portion 12, the nasal expiration collecting portion 11 branches off into a first nasal expiration collecting portion 111 and a second nasal expiration collecting portion 112.

Each of the first and second nasal expiration collecting portions 111, 112 is configured by a fluid path having an approximately cylindrical shape. When the airway adaptor 1 is attached to the human body, tip end portions of the first and second nasal expiration collecting portions 111, 112 are inserted into the two nostrils of the human body, respectively. The nasal expiration collecting portion 11 collects the expiration which is emitted from the nasal cavity of the human body, toward the gas sensor attaching portion 12. Alternatively, the nasal expiration collecting portion 11 may send gasses which are supplied from the first and second gas supplying portions 131, 132, to the nostrils of the human body.

The first nasal expiration collecting portion 111 may include a first locked portion 113 in the vicinity of a tip end part of the front surface side. Moreover, the second nasal expiration collecting portion 112 may include a second locked portion 114 in the vicinity of a tip end part of the front surface side. Both the first and second locked portions 113, 114 are configured by through holes which are formed in the first and second nasal expiration collecting portions 111, 112, respectively.

The gas sensor attaching portion 12 may include a base portion 121, a gas sensor engaging portion 122, a magnet portion 123, gas sensor locking portions 124, gas sensor measurement windows 125, a first locking portion 127, and a second locking portion 128.

The base portion 121 forms an approximate shape of the gas sensor attaching portion 12, and supports the nasal expiration collecting portion 11 which is disposed on the gas sensor attaching portion 12.

The gas sensor engaging portion 122 is disposed so as to be engaged with the gas sensor 30. The gas sensor engaging portion 122 has a shape with which an engaged portion of the gas sensor 30 can be engaged. Specifically, the gas sensor engaging portion 122 has a partition wall which separates the outer and inner sides from each other, on each of at least the front surface and the both side surfaces, thereby forming the gas passage portion, into which an expiration from the nasal expiration collecting portion 11 and the oral expiration collecting portion 20 flows, in the inner space.

The magnet portion 123 can be contacted with a magnet portion which is disposed in the engaged portion of the gas sensor 30. The magnet portion 123 is disposed in, for example, the front-oriented surface of the gas sensor engaging portion 122. The magnet portion 123 is contacted with the magnet portion of the gas sensor 30 which is not illustrated, to prevent the gas sensor 30 from slipping off.

The gas sensor locking portion 124 has a shape which, in order to allow locking with at least a part of the housing of the gas sensor 30, can receive a part of the housing of the gas sensor.

The gas sensor measurement windows 125 are disposed so that the concentration of carbon dioxide of the gas in the gas passage portion formed in the gas sensor engaging portion 122 is measured by the gas sensor 30 which is attached to the gas sensor attaching portion 12. Therefore, the gas sensor measurement windows 125 are formed so that light emitted from the emitter of the gas sensor 30, and light propagating to the detector can pass through the respective windows. The gas sensor measurement windows 125 are windows in which, for example, a predetermined light transmittance is ensured. The gas sensor measurement windows 125 are disposed at respective positions which, when the gas sensor 30 is attached as illustrated in FIG. 1, correspond to the positions of the emitter and the detector, such as the two opposing partition walls of the side surfaces forming the gas sensor engaging portion 122.

Figure 3:
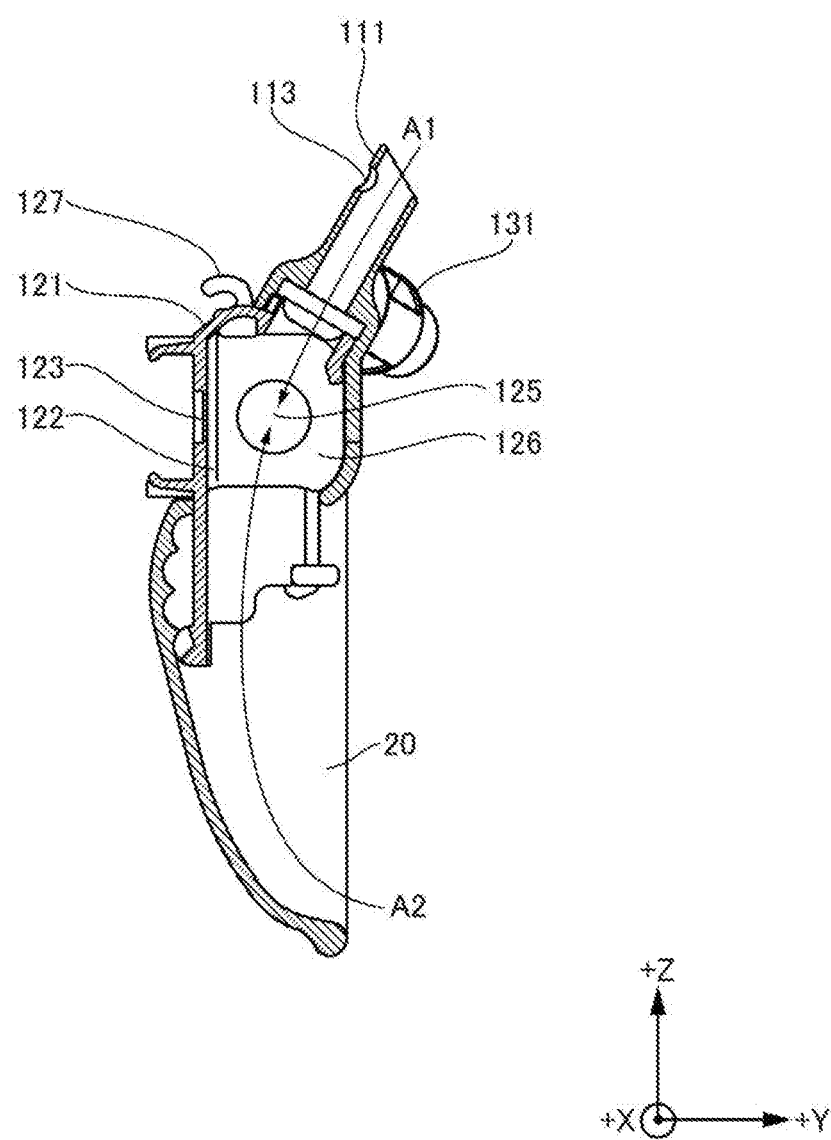
FIG. 3 is a longitudinal sectional view illustrating the internal structure of the airway adaptor illustrated in FIG. 1, as viewed in the right lateral direction.

FIG. 3 is a longitudinal sectional view illustrating the internal structure of the airway adaptor 1, as viewed in the right lateral direction. In order to illustrate the internal structure of the airway adaptor 1, FIG. 3 illustrates sections of the first nasal expiration collecting portion 111, the gas sensor engaging portion 122, the gas passage portion 126, and the oral expiration collecting portion 20. As illustrated in FIG. 3, the gas passage portion 126 is formed in the gas sensor engaging portion 122. The gas passage portion 126 is disposed inside the partition walls of the gas sensor engaging portion 122. The gas passage portion 126 functions as a gas passage for the expiration which is indicated by the arrow A1 in FIG. 3, and which is emitted from the nasal expiration collecting portion 11, and for the expiration which is indicated by the arrow A2, and which is collected by the oral expiration collecting portion 20. The expiration which is collected in the gas passage portion 126 is subjected to a measurement of $CO_2$ by the gas sensor 30 which is attached to the gas sensor engaging portion 122.

The first locking portion 127 is disposed on the base portion 121. The first locking portion 127 is configured by a projection which is projected on the base portion 121. The first locking portion 127 is formed as a projection having a size which corresponds to the size of the hole of the first locked portion 113. The first locking portion 127 may be formed into a hook-like shape in order to maintain the locked state of the locked first locked portion 113.

In the same or similar manner as the first locking portion 127, the second locking portion 128 is disposed on the base portion 121. In the same or similar manner as the first locking portion 127, preferably, the second locking portion 128 may be configured by a projection which is projected on the base portion 121, and have the size and shape which are same as or similar to those of the first locking portion 127.

As illustrated in FIGS. 1 to 3, the gas supplying portion may include a first gas supplying portion 131, a second gas supplying portion 132, a first tube connecting portion 133, and a second tube connecting portion 134.

The first gas supplying portion 131 is configured by a fluid path for supplying a gas to the nasal expiration collecting portion 11. The first gas supplying portion 131 is disposed on the left side as viewed toward the face of the human body. In the same or similar manner as the first gas supplying portion 131, also the second gas supplying portion 132 is configured by a fluid path for supplying a gas to the nasal expiration collecting portion 11. The second gas supplying portion 132 is disposed on the right side as viewed toward the face of the human body.

The first tube connecting portion 133 is disposed in an end part of the first gas supplying portion 131. A tube which is not illustrated, and through which the gas is supplied can be connected to the first tube connecting portion 133. The first tube connecting portion 133 is configured by an opening which communicates with the first gas supplying portion 131. The gas which is supplied through the tube connected to the first tube connecting portion 133 is supplied to the nasal cavity of the human body from the nostril with passing through the nasal expiration collecting portion 11 from the first gas supplying portion 131.

The second tube connecting portion 134 is disposed in an end part of the second gas supplying portion 132. In the same or similar manner as the first tube connecting portion 133, the tube through which the gas is supplied can be connected to the second tube connecting portion 134. The second tube connecting portion 134 is configured by an opening which communicates with the second gas supplying portion 132. The gas which is supplied through the tube connected to the second tube connecting portion 134 is supplied to the nasal cavity of the human body from the nostril with passing through the nasal expiration collecting portion 11 from the second gas supplying portion 132.

Figure 4:
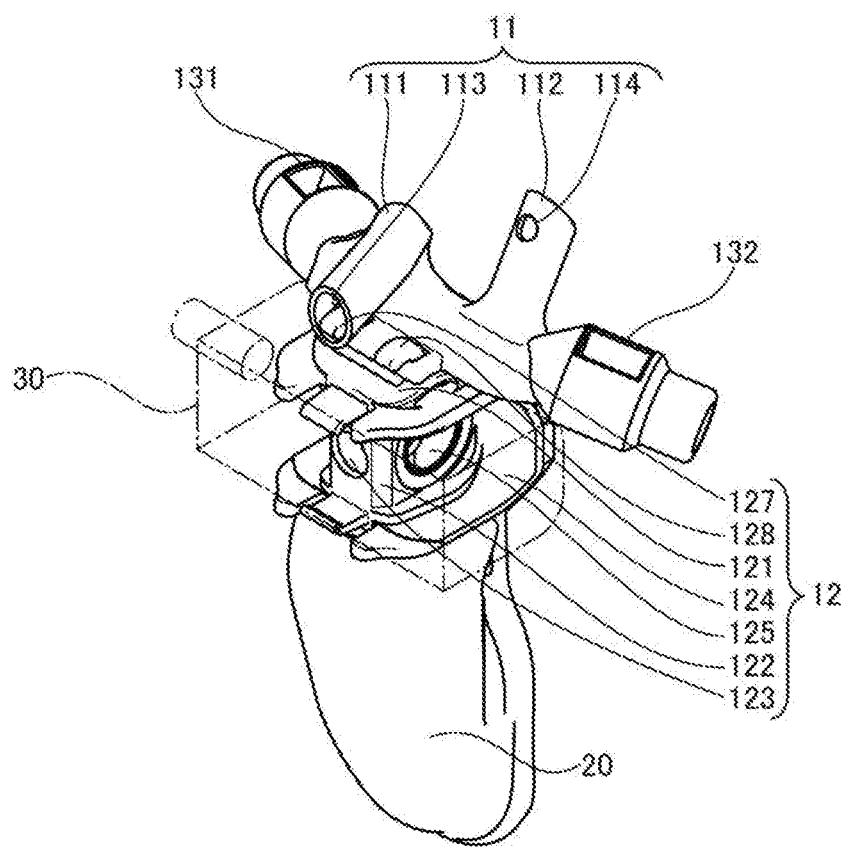
FIG. 4 is a perspective view illustrating a manner of obstructing a first nasal expiration collecting portion of the airway adaptor illustrated in FIG. 1.

FIG. 4 is a perspective view illustrating a manner of obstructing the first nasal expiration collecting portion 111 of the airway adaptor 1. FIG. 4 illustrates a manner in which the first nasal expiration collecting portion 111 of the nasal expiration collecting portion 11 is bent in the −Y direction, and the first locked portion 113 is locked to the first locking portion 127, thereby obstructing the first nasal expiration collecting portion 111.

In the airway adaptor 1, as described above, the nasal expiration collecting portion 11 is formed by a flexible material. In the airway adaptor 1, the first locked portion 113 is disposed in the first nasal expiration collecting portion 111, and the second locked portion 114 is disposed in the second nasal expiration collecting portion 112. In the airway adaptor 1, as described above, moreover, the first and second locking portions 127, 128 are disposed in the base portion 121 of the gas sensor attaching portion 12 which is on the front side. In the airway adaptor 1, the first locked portion 113 is locked to the first locking portion 127, and the second locked portion 114 is locked to the second locking portion 128, thereby the first and second nasal expiration collecting portions 111, 112 which are formed by a soft and flexible member are bent. As a result, the flow paths of the first and second nasal expiration collecting portions 111, 112 are collapsed, and the states of the flow paths are changed from the flowing state where the flow of the expiration is allowed, to the obstruction state where the flow of the expiration is blocked.

In the airway adaptor 1, as described above, the first and second locked portions 113, 114 function as the obstruction state producing portion which causes the first nasal expiration collecting portion 111 to be obstructable. In the airway adaptor 1, moreover, the first and second locking portions 127, 128 function as the obstruction state producing portion which causes the second nasal expiration collecting portion 112 to be obstructable. In the airway adaptor 1, then, the first and second nasal expiration collecting portions 111, 112 of the nasal expiration collecting portion 11 can show the flowing state where the flow of the expiration is allowed, and the obstruction state where the flow of the expiration is blocked.

[Use Examples of Airway Adaptor]

Next, use examples of the airway adaptor 1 which has been described above will be described.

Figure 5:
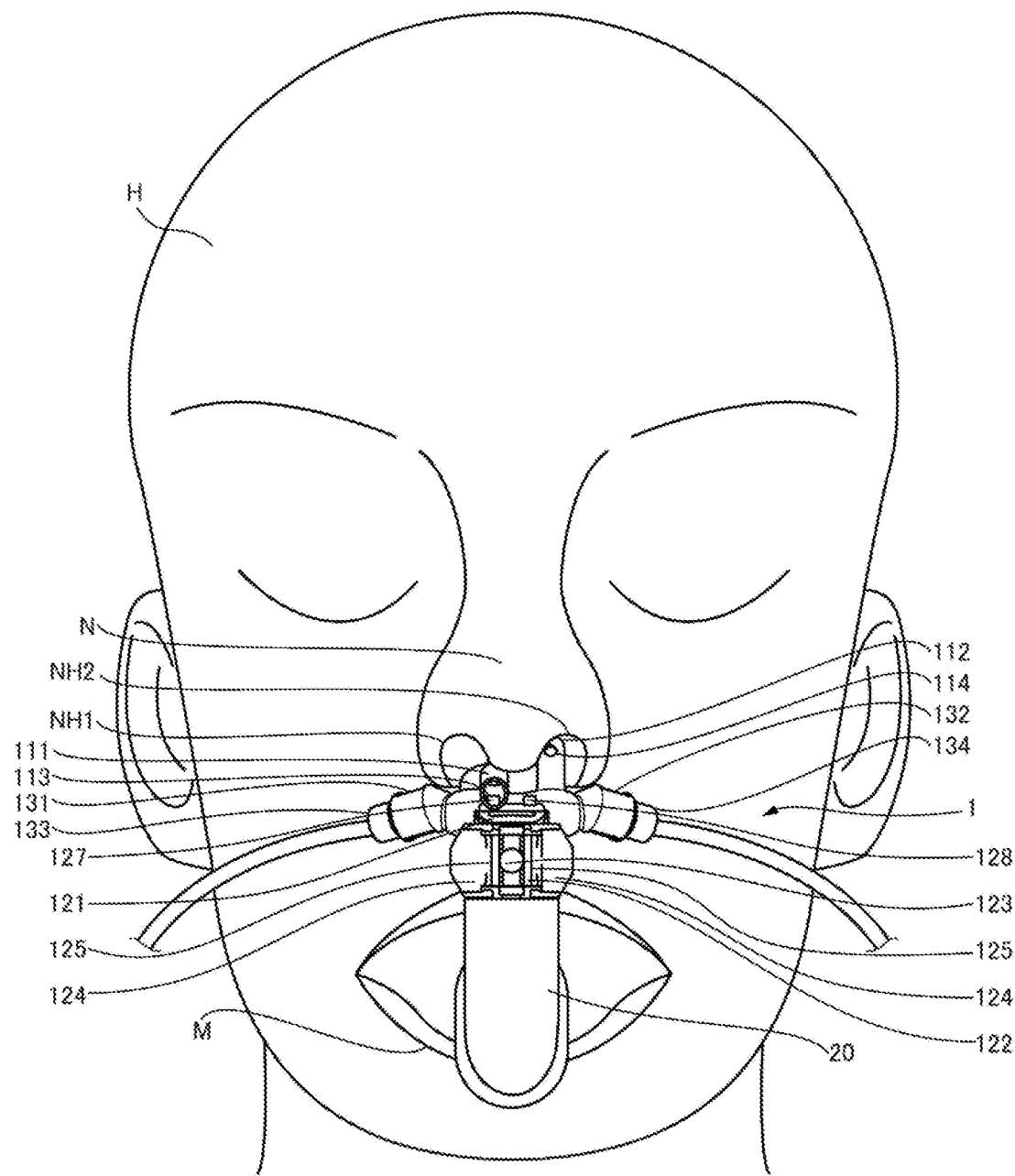
FIG. 5 is a diagram illustrating a state where the airway adaptor illustrated in FIG. 1 is attached to the human body.

FIG. 5 is a diagram illustrating a state where the airway adaptor 1 is attached to the human body H. In the airway adaptor 1, in such a case where, when the adaptor is attached to the human body H, a tool for a transnasal endoscopic surgical procedure is to be inserted through one nostril NH1 as illustrated in FIG. 5, the first locked portion 113 is locked to the first locking portion 127, thereby the first nasal expiration collecting portion 111 can be obstructed.

According to the airway adaptor 1, when a tool is to be inserted into the nostril NH1, as described above, the nasal expiration collecting portion 11 can be prevented from impeding the implementation of techniques, and the adaptability to the techniques can be improved.

According to the airway adaptor 1 which can be used in this way, even under circumstances where a liquid such as snivel or medicine drips from the nostril NH1, the first nasal expiration collecting portion 111 can be obstructed. Therefore, it is possible to prevent a situation where a liquid enters the gas passage portion 126 to cause the gas sensor 30 to malfunction, from occurring.

In the nasal expiration collecting portion 11, the positions where the first and second locked portions 113, 114 are respectively disposed are not limited to the above-described ones. The first and second locked portions 113, 114 are requested only to lock the flexible nasal expiration collecting portion 11 to maintain the bent state, so that the nasal expiration collecting portion 11 is obstructed.

In the airway adaptor 1, the gas supplying portion is not limited to have the configuration where two portions are laterally separated as viewed toward the face of the human body, such as in the case of the first and second gas supplying portions 131, 132. For example, the gas supplying portion may have a configuration where the gas is suppled through a tube which is connected to one tube connecting portion.

[Second Embodiment]

Next, a second embodiment of the airway adaptor of the presently disclosed subject matter will be described. In the description of the embodiment, only differences with the airway adaptor 1 of the above-described embodiment will be described.

Figure 6:
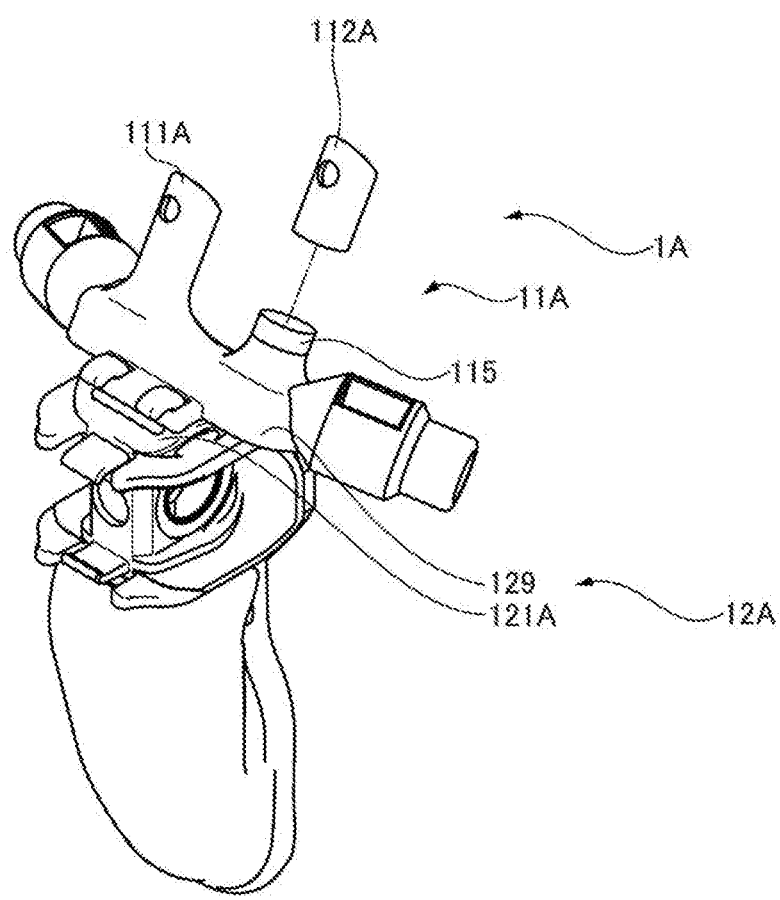
FIG. 6 is a perspective view illustrating a second embodiment of the airway adaptor of the presently disclosed subject matter.

FIG. 6 is a perspective view illustrating the second embodiment of the airway adaptor of the presently disclosed subject matter. In the airway adaptor 1A of the embodiment, as illustrated in FIG. 6, the configurations of a nasal expiration collecting portion 11A and a gas sensor attaching portion 12A are different from those of the nasal expiration collecting portion 11 and gas sensor attaching portion 12 of the above-described airway adaptor 1.

In the nasal expiration collecting portion 11A, a first nasal expiration collecting portion 111A and a second nasal expiration collecting portion 112A are formed so as to be detachable from the airway adaptor 1. FIG. 6 illustrates a state where only the second nasal expiration collecting portion 112A is detached from the airway adaptor 1.

The first and second nasal expiration collecting portions 111A, 112A are attached onto a tubular attached portion 129 which is disposed in a base portion 121A of the gas sensor attaching portion 12A, thereby the nasal expiration collecting portions are attached to the airway adaptor 1A.

A lid 115 which functions as the obstruction state producing portion is attached to the attached portion 129 from which the first nasal expiration collecting portion 111A or the second nasal expiration collecting portion 112A is detached, so that the gas passage of the corresponding nasal expiration collecting portion can be obstructed.

In the airway adaptor 1A, as described above, the first nasal expiration collecting portion 111A or the second nasal expiration collecting portion 112A is detached, and the resulting opening is closed by the lid 115, thereby the nasal expiration collecting portion 11A can be prevented from impeding the implementation of techniques such as insertion of a tool into the other nostril. According to the airway adaptor 1A, therefore, the adaptabilities to the techniques can be improved.

[Third Embodiment]

Next, a third embodiment of the airway adaptor of the presently disclosed subject matter will be described. In the description of the embodiment, only differences with the airway adaptor 1 of the above-described embodiment will be described.

Figure 7:
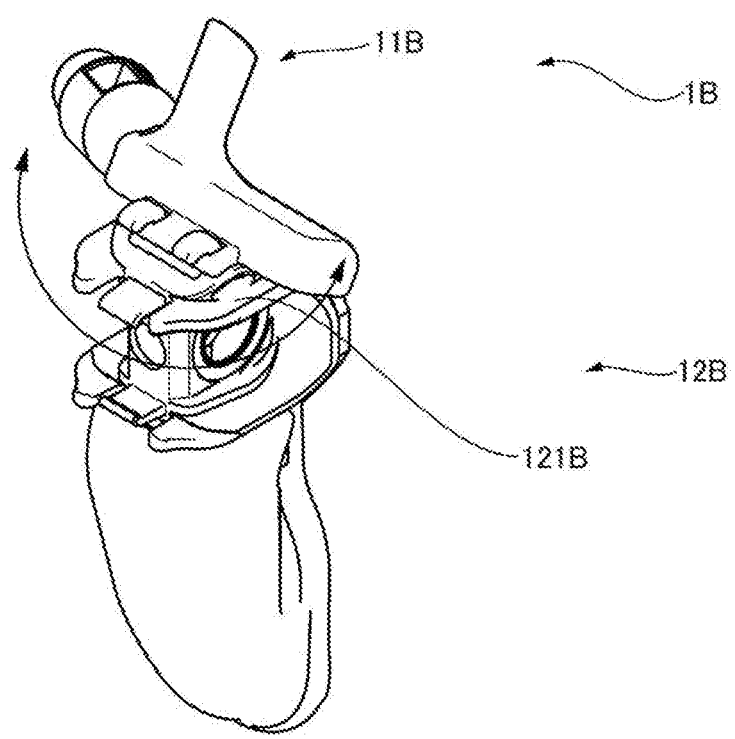
FIG. 7 is a perspective view illustrating a third embodiment of the airway adaptor of the presently disclosed subject matter.

FIG. 7 is a perspective view illustrating the third embodiment of the airway adaptor of the presently disclosed subject matter. In the airway adaptor 1B of the embodiment, as illustrated in FIG. 7, the configurations of a nasal expiration collecting portion 11B and a gas sensor attaching portion 12B are different from those of the nasal expiration collecting portion 11 and gas sensor attaching portion 12 of the above-described airway adaptor 1.

Unlike the nasal expiration collecting portion 11 including the first and second nasal expiration collecting portions 111, 112, the nasal expiration collecting portion 11B may include one tubular part which can be inserted into the nostril. The nasal expiration collecting portion 11B is configured so as to swing about the Z direction with respect to a base portion 121B of the gas sensor attaching portion 12B. As illustrated in FIG. 7, therefore, the nasal expiration collecting portion 11B may be deviated to the left side as opposed to the human body so as to be easily inserted into the right nostril of the human body.

Figure 8:
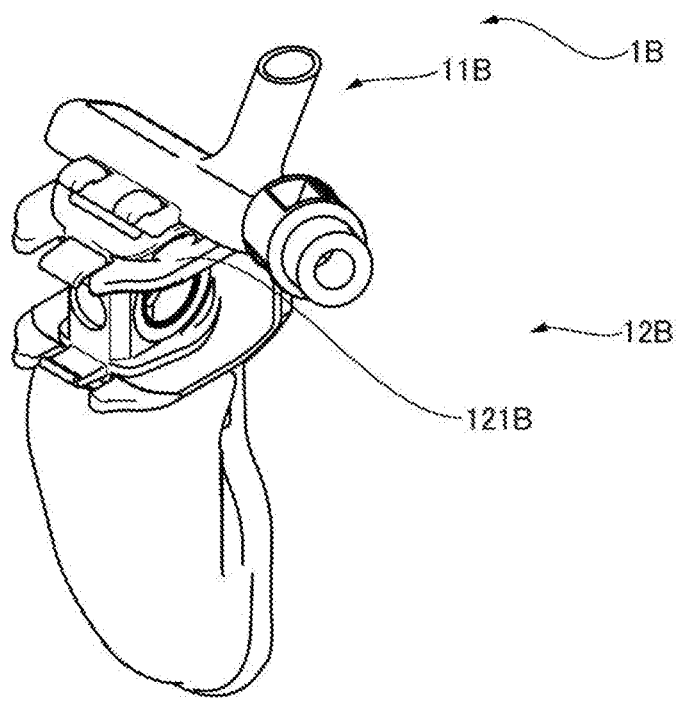
FIG. 8 is a perspective view illustrating another mode of the airway adaptor illustrated in FIG. 7.

FIG. 8 is a perspective view illustrating another mode of the airway adaptor 1B. When the nasal expiration collecting portion 11B is swung with respect to the base portion 121B, the nasal expiration collecting portion 11B may be deviated to the right side as opposed to the human body as illustrated in FIG. 8 so as to be easily inserted into the left nostril of the human body.

Although FIGS. 7 and 8 illustrate the examples in which the whole nasal expiration collecting portion 11B including the gas supplying portion is swung with respect to the base portion 121B, the presently disclosed subject matter is not limited to this. For example, the nasal expiration collecting portion 11B may be configured so that only the portion which connects the cylindrical part that is to be inserted into the nostril, to the gas passage portion 126 can be swung, and the gas supplying portion cannot be swung.

In the airway adaptor 1B, as described above, the one nasal expiration collecting portion 11B is deviated to the side of the one nostril, thereby the nasal expiration collecting portion 11B can be prevented from impeding the implementation of techniques such as insertion of a tool into the other nostril, and the adaptabilities to the techniques can be improved.

[Fourth Embodiment]

Next, a fourth embodiment of the airway adaptor of the presently disclosed subject matter will be described. In the description of the embodiment, only differences with the airway adaptor 1 of the above-described embodiment will be described.

Figure 9:
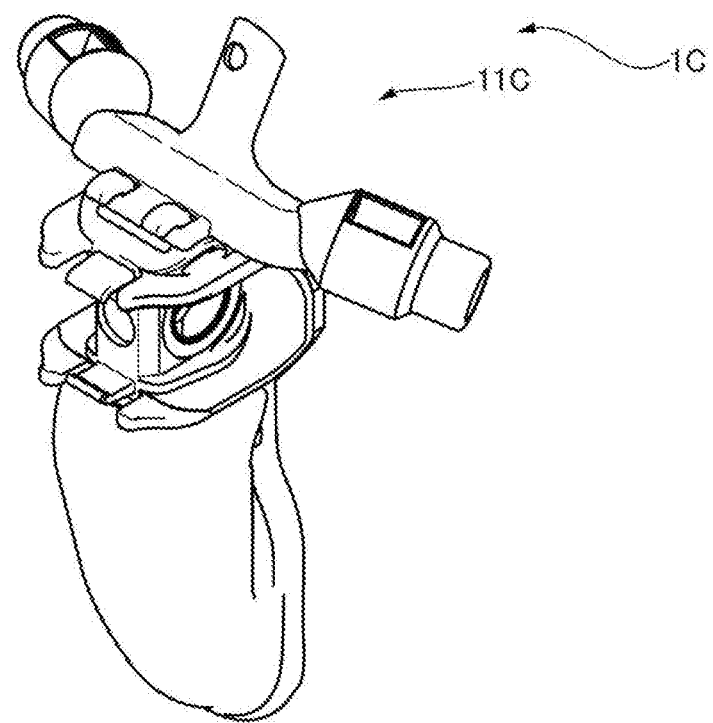
FIG. 9 is a perspective view illustrating a fourth embodiment of the airway adaptor of the presently disclosed subject matter.

FIG. 9 is a perspective view illustrating the fourth embodiment of the airway adaptor of the presently disclosed subject matter. In the airway adaptor 1C of the embodiment, as illustrated in FIG. 9, the configuration of a nasal expiration collecting portion 11C is different from that of the nasal expiration collecting portion 11 of the above-described airway adaptor 1.

Unlike the nasal expiration collecting portion 11 including the first and second nasal expiration collecting portions 111, 112, the nasal expiration collecting portion 11C may include one tubular part which can be inserted into the nostril. When the airway adaptor 1C is to be attached to the human body, the nasal expiration collecting portion 11C is inserted into one of the two nostrils. No technique is applied to the one nostril. In this case, the nasal expiration collecting portion 11C may be larger in tube length than the above-described nasal expiration collecting portion 11 and the like.

In the airway adaptor 1C, as described above, the one nasal expiration collecting portion 11C is inserted into one of the nostrils, thereby the nasal expiration collecting portion 11C can be prevented from impeding the implementation of technique such as insertion of a tool into the other nostril, and the adaptabilities to the techniques can be improved.

[Fifth Embodiment]

Next, an embodiment of the nasal cannula of the presently disclosed subject matter will be described as a fifth embodiment. In the description of the embodiment, only differences with the airway adaptor 1 of the above-described embodiment will be described.

Figure 10:
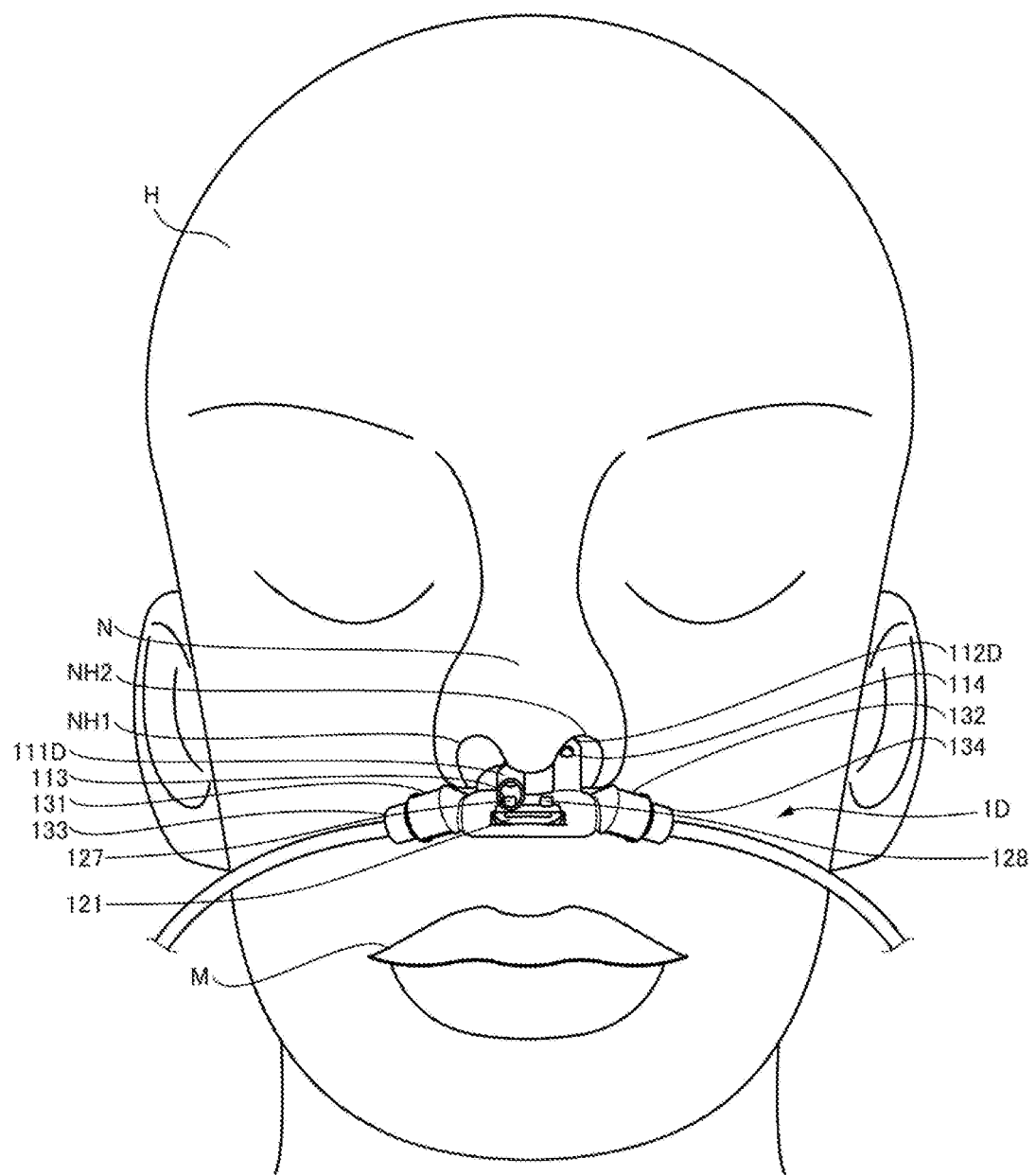
FIG. 10 is a diagram illustrating an embodiment of the nasal cannula of the presently disclosed subject matter, in a state where the nasal cannula is attached to the human body.

FIG. 10 is a diagram illustrating the embodiment of the nasal cannula 1D of the presently disclosed subject matter, in a state where the nasal cannula 1D is attached to the human body H. As illustrated in FIG. 10, the nasal cannula 1D may include a first nostril connecting portion 111D, a second nostril connecting portion 112D, the first locked portion 113, the second locked portion 114, the base portion 121, the first locking portion 127, the second locking portion 128, the first gas supplying portion 131, and the second gas supplying portion 132.

The first nostril connecting portion 111D is connected to the left nostril NH1 of the human body H to supply the gas to the nasal cavity. The second nostril connecting portion 112D is connected to the right nostril NH2 of the human body H to supply the gas to the nasal cavity. The configuration of the first nostril connecting portion 111D, including the disposition of the first locked portion 113 which is lockable to the first locking portion 127 is same as or similar to that of the above-described first nostril connecting portion 111. Moreover, the configuration of the second nostril connecting portion 112D, including the disposition of the second locked portion 114 which is lockable to the second locking portion 128 is same as or similar to that of the above-described second nostril connecting portion 112. The base portion 121 forms an approximate shape of the nasal cannula 1D. The base portion 121 supports the nostril connecting portion having the first and second nostril connecting portion 111D, 112D, and the gas supplying portion having the first and second gas supplying portions 131, 132. The first and second locking portions 127, 128 are configured by projections which are projected on the base portion 121, respectively, in the same or similar manner as the first and second locking portions 127, 128 of the above-described airway adaptor 1.

The first gas supplying portion 131 supplies the gas to the first nostril connecting portion 111D. The second gas supplying portion 132 supplies the gas to the second nostril connecting portion 112D.

In the nasal cannula 1D, in the same or similar manner as the airway adaptor 1, in such a case where, when the cannula is attached to the human body H, a tool for a transnasal endoscopic surgical procedure is to be inserted through one nostril NH1 as illustrated in FIG. 10, the first locking portion 127 can be locked to the first locked portion 113. According to the nasal cannula 1D, therefore, the first nostril connecting portion 111D can be obstructed in the same or similar manner as the airway adaptor 1 which includes the first locking portion 127 and the first locked portion 113. In the nasal cannula 1D, in the same or similar manner as the airway adaptor 1, in such a case where, when the cannula is attached to the human body H, a tool for a transnasal endoscopic surgical procedure is to be inserted through the other nostril NH2, the second locking portion 128 can be locked to the second locked portion 114. In the nasal cannula 1D, namely, the first nostril connecting portion 111D and the first locking portion 127, and the second nostril connecting portion 112D and the second locking portion 128 function as the obstruction state producing portion which causes the corresponding nostril connecting portion formed by a flexible member, to be bent, thereby obstructing the nostril connecting portion. According to the nasal cannula 1D, therefore, the second nostril connecting portion 112D can be obstructed in the same or similar manner as the airway adaptor 1 including the second locking portion 128 and the second locked portion 114.

According to the nasal cannula 1D, when a tool is to be inserted into the nostril NH1 or NH2, as described above, the first nostril connecting portion 111D or the second nostril connecting portion 112D can be prevented from impeding the implementation of techniques, and the adaptability to the techniques can be improved.

What is claimed is:

1. A nasal cannula comprising:
a nostril connecting portion which is configured to be connected to a nostril of a living body, and which supplies a gas to a nasal cavity; and
a base portion which supports the nostril connecting portion,
wherein the nostril connecting portion produces a flowing state where a flow of the gas is allowed, and an obstruction state where the flow of the gas is blocked,
wherein the nostril connecting portion is formed by a flexible member, and comprises an obstruction state producing portion that bends the nostril connecting portion to obstruct the nostril connecting portion, and
wherein the obstruction state producing portion comprises:
a locked portion that is a hole which is formed in the nostril connecting portion; and
a locking portion that is a projection formed on the base portion and that is engaged with the locked portion to maintain a state where the nostril connecting portion is bent.

2. The nasal cannula according to claim 1, wherein the nostril connecting portion comprises:
a first nostril connecting portion which is configured to be connected to one nostril of the living body; and
a second nostril connecting portion which is configured to be connected to another nostril of the living body.

* * * * *